United States Patent
Cecchi et al.

(10) Patent No.: US 6,858,629 B1
(45) Date of Patent: Feb. 22, 2005

(54) HETEROARYLOXY PROPANOLAMINES, PREPARATION METHOD AND PHARMACEUTICAL COMPOSITIONS CONTAINING SAME

(75) Inventors: Roberto Cecchi, Lodi (IT); Ambrogio Oliva, Sarrono (IT)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 10/070,453

(22) PCT Filed: Sep. 8, 2000

(86) PCT No.: PCT/FR00/02482

§ 371 (c)(1),
(2), (4) Date: Mar. 6, 2002

(87) PCT Pub. No.: WO01/17989

PCT Pub. Date: Mar. 15, 2001

(30) Foreign Application Priority Data

Sep. 8, 1999 (FR) .............................. 99 11204

(51) Int. Cl.$^7$ .................... A61K 31/445; C07D 401/06; C07D 211/06
(52) U.S. Cl. ....................... 514/318; 514/323; 546/193; 546/199; 549/512
(58) Field of Search ............................. 514/318, 323; 546/193, 199; 549/512

(56) References Cited

U.S. PATENT DOCUMENTS 6,444,685 B1 * 9/2002 Sum et al. .................. 514/317
6,506,901 B2 * 1/2003 Steffan et al. .............. 546/192

FOREIGN PATENT DOCUMENTS

DE  35 24 955 A  1/1986
EP  0 095 454 A  11/1983

OTHER PUBLICATIONS

Fisher et al. "Substituted sulfonamides . . . " Ca 125:221588 (1996).*
Dennedy et al. "Beta–3 versus beta–2 adrenergic . . . " CA 135:267188 (2001).*
Brazzell et al. Treatment of glaucoma and ocular . . . Ca 126:1213 (1996).*
Boyer et al. "use of beta adrenergic . . . " CA 124:194336 (1996).*
Hori, M. et al., Journal of Organic Chemistry, 1998, vol. 63, No. 3, pp 889–894.
Derwent Patent Abstract No. 198605 (2002).
Derwent Patent Abstract No. 198349 (2002).

* cited by examiner

*Primary Examiner*—Celia Chang
(74) *Attorney, Agent, or Firm*—Michael D. Alexander

(57) ABSTRACT

Compounds of formula (I):

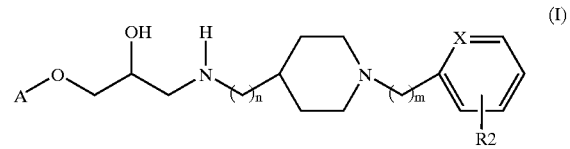

where X is N or CH;
A represents a group of formula (a) or (b)

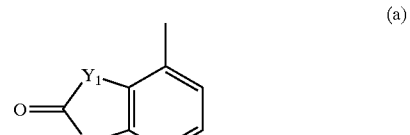

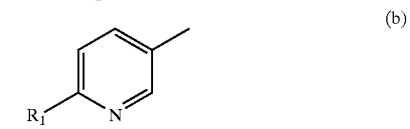

$R_1$ represents hydrogen or an —$NH_2$, —$NR_3R_4$, —$NR_3CO(C_1$–$C_4)$Alk or —$NR_3SO_2(C_1$–$C_4)$Alk group;
$R_2$ represents hydrogen, a halogen or a $(C_1$–$C_4)$Alk, $(C_1$–$C_4)$ alkoxy, —COOH, —COO$(C_1$–$C_4)$Alk, —CN, —CONR$_3$R$_4$, —NO$_2$, —SO$_2$NR$_3$R$_4$ or —NHSO$_2$ $(C_1$–$C_4)$Alk;
m and n each represent 0, 1 or 2;
$R_3$ and $R_4$ each represent hydrogen or a $(C_1$–$C_4)$Alk group;
$Y_1$ and $Y_2$ each represent NH or O;
and their salts or solvates, a process for their preparation and the pharmaceutical compositions comprising them.

25 Claims, No Drawings

HETEROARYLOXY PROPANOLAMINES, PREPARATION METHOD AND PHARMACEUTICAL COMPOSITIONS CONTAINING SAME

The present invention relates to novel propanolamines, to the pharmaceutical compositions comprising them, to a process for their preparation and to intermediates in this process.

These novel compounds have shown an agonist activity with respect to the $\beta_3$ receptor and thus can be used in the treatment of pathologies which benefit from the activation of this receptor.

BE 902897 discloses aryloxypropanolamines carrying a 1-substituted-4-piperidininyl group on the amine, these compounds having a $\beta_1$-blocking and $\alpha$-blocking activity.

J. Org. Chem., 1988, 63, 889–894, describes other aryloxypropanolamines carrying a 1-substituted-4-piperidinyl group on the amine.

It has now been found that heteroaryloxy-propanolamines carrying a piperidin-4-yl or piperidin-4-ylalkylene radical on the amine have an agonist activity with respect to $\beta_3$-adrenergic receptors.

Thus, the present invention relates, according to one of its aspects, to propanolamines of formula (I)

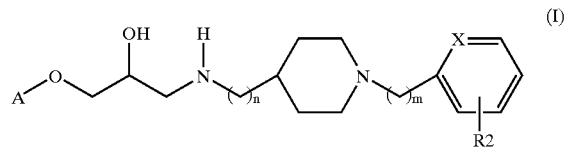

(I)

where X is N or CH;
A represents a group of formula (a) or (b)

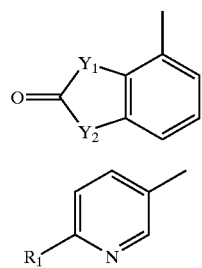

$R_1$ represents a hydrogen atom or an —NH$_2$, —NR$_3$R$_4$, —NR$_3$CO(C$_1$–C$_4$)Alk or —NR$_3$SO$_2$(C$_1$–C$_4$)Alk group;
$R_2$ represents a hydrogen or halogen atom or a (C$_1$–C$_4$)Alk, (C$_1$–C$_4$)alkoxy, —COOH, —COO(C$_1$–C$_4$)Alk, —CN, —CONR$_3$R$_4$, —NO$_2$, —SO$_2$NR$_3$R$_4$ or —NHSO$_2$(C$_1$–C$_4$)Alk group;
m and n each represent 0, 1 or 2;
$R_3$ and $R_4$ each represent a hydrogen atom or a (C$_1$–C$_4$)Alk group;
$Y_1$ and $Y_2$ each represent NH or O;
and their salts or solvates.

In the present description, the term "(C$_1$–C$_4$)Alk" denotes a monovalent radical of a saturated straight- or branched-chain C$_1$–C$_4$ hydrocarbon.

The salts of the compounds of formula (I) according to the present invention comprise both addition salts with pharmaceutically acceptable inorganic or organic acids, such as the hydrochloride, hydrobromide, sulfate, hydrogensulfate, dihydrogen-phosphate, citrate, maleate, tartrate, fumarate, gluconate, methanesulfonate, 2-naphthalenesulfonate, and the like, and addition salts which make possible suitable separation or crystallization of the compounds of formula (I), such as the picrate or oxalate, or addition salts with optically active acids, for example camphorsulfonic acids and mandelic or substituted mandelic acids.

Furthermore, when the compounds of formula (I) have a free carboxyl group, the salts also comprise the salts with inorganic bases, preferably the salts obtained with bases derived from alkali metals, such as sodium or potassium, or with organic bases.

The optically pure stereoisomers and the mixtures of isomers of the compounds of formula (I) form part of the present invention.

Preferred compounds of the present invention comprise the compounds of formula (I) where X represents CH.

Other preferred compounds of the present invention are those where X represents nitrogen and the $R_2$ group is in the 5-position.

Other preferred compounds are those where the (C$_1$–C$_4$)Alk group is a methyl or ethyl group.

Other preferred compounds are those where $R_2$ is chosen from —COOH, —COO(C$_1$–C$_4$)Alk, —CN, —NO$_2$, —CONR$_3$R$_4$, —NHSO$_2$—(C$_1$–C$_4$)Alk and Cl.

Other compounds preferred still are those where n and m are each zero.

The optionally salified compound 3-[1-(5-ethoxycarbonylpyrid-2-yl)-4-piperidinylamino]-1-[1,2-dihydro-2-oxobenzimidazol-4-yloxy]-2-propanol is particularly advantageous.

Another particularly advantageous compound is optionally salified 3-[1-(5-ethoxycarbonylpyrid-2-yl)-4-piperidinylamino]-1-[2-aminopyrid-5-yloxy]-2-propanol.

The compounds of formula (I) are prepared by treating an epoxide of formula (II):

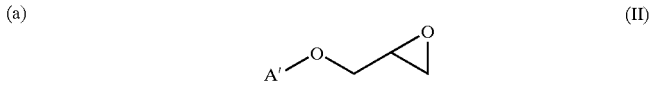

(II)

where A' represents the group (a) or the group (b) in which $R_1$ is optionally protected by a protective group, with an amine of formula (III):

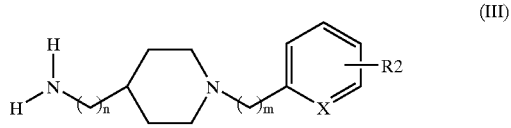

(III)

where m, n, $R_2$ and X are as indicated above, the protective group optionally present being removed and the product of formula (I) thus obtained being converted into one of its salts or solvates.

Alternatively, when A represents a group (b) and $R_1$ is an NH$_2$ group, the compounds of formula (I) are preferably prepared by condensation of an amine of formula (III) with a product of formula (II) where A' is the group (b) and $R_1$ is a group of formula:

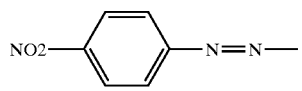

and by subjecting the product of formula (IV) thus obtained:

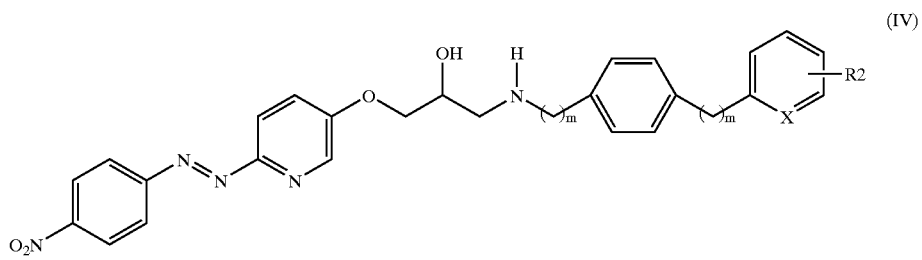

(IV)

to a hydrogenation reaction in order to convert the 4-nitrophenyldiazenyl group to an amino group, and optionally the product of formula (I) thus obtained is converted into one of its salts or solvates.

When A is a group of formula (a) and $Y_1$ and $Y_2$ represent a nitrogen atom, it is also possible to prepare the compounds of formula (I) by treating a compound of formula (V):

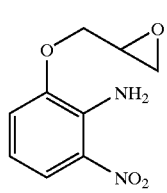

(V)

with an amine of formula (III), by reducing the nitro group of the product of formula (VI) thus obtained:

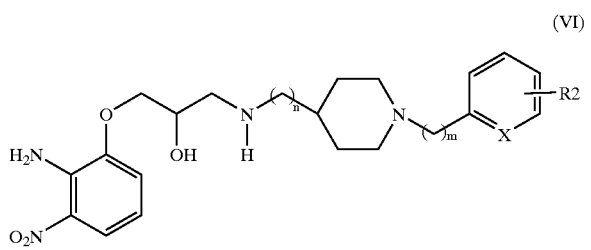

(VI)

and by treating the product of formula (VII) thus obtained:

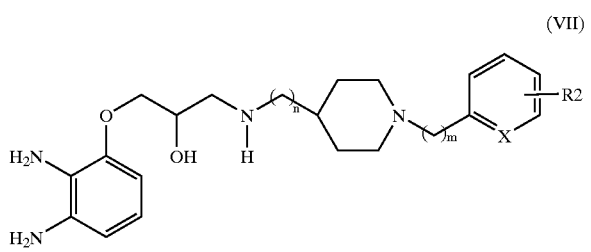

(VII)

with a carbonylation agent, namely an agent capable of inserting a carbonyl group into the molecule, such as, for example, carbonyldiimidazole or phosgene, to produce the final product, which can optionally be converted into one of its salts or solvates.

The reaction for the reduction of the nitro group to an amino group can be carried out, for example, by catalytic hydrogenation. Use may be made, as reaction solvent, of, for example, a polar protic solvent, such as water, acetic acid or an alcohol, for example ethanol, methanol or isopropanol, an ester, for example ethyl acetate, a linear or cyclic ether, for example tetrahydrofuran or dioxane, or an aromatic solvent, for example benzene or toluene.

The cyclization reaction is preferably carried out using carbonyldiimidazole in an inert solvent, such as tetrahydrofuran or a linear ether, at a temperature of between ambient temperature and the reflux temperature of the solvent chosen.

The reaction between the epoxides and the amine (III) is carried out in an organic solvent, such as a lower alcohol, for example methanol, ethanol or isopropanol; dimethyl sulfoxide; a linear or cyclic ether; or an amide, for example dimethylformamide or dimethylacetamide, and by using at least equimolecular amounts of the reactants, optionally a slight excess of amine.

The reaction temperature is between ambient temperature and the reflux temperature of the solvent chosen.

The compounds of formula (II) in which A' is a group (a) can be prepared according to the general process disclosed in scheme III of WO97/10825 or according to Patent DE 2700193.

The compounds of formula (II) where A' is a group (b) can be prepared according to the general process disclosed in EP 0 611 003.

The amines of formula (III) can be prepared by reaction of the appropriate synthons of formula (VIII):

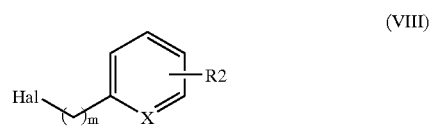

(VIII)

where Hal represents a halogen and $R_2$, m and X are as defined above, with a piperidine of formula (IX):

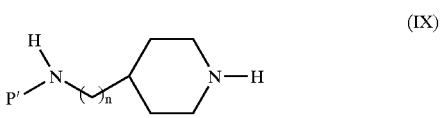

(IX)

where n is as defined above and P' represents a protective group, in an organic solvent, in the presence of a base, followed by the removal of the P' group from the compounds of formula (X) thus obtained:

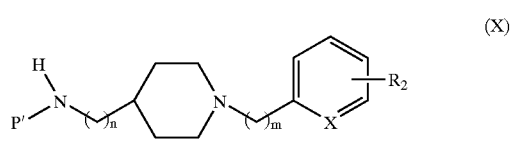

(X)

Use may be made, as reaction solvent, of, for example, dimethylformamide, pyridine, dimethyl sulfoxide, a linear or cyclic ether or a chlorinated solvent, such as dichloromethane.

Use may be made, as base, of, for example, an alkaline hydroxide, an alkaline carbonate, such as potassium carbonate, or a tertiary amine, such as triethylamine.

The above condensation reaction is complete in a few hours, normally in 2 to 12 hours.

The reaction temperature is between ambient temperature and the reflux temperature of the solvent chosen.

Use may be made, as protective groups P', of acyl groups, such as formyl, acetyl, propionyl, phenylacetyl, phenoxyacetyl and the like; an alkoxy-carbonyl group, such as tert-butoxycarbonyl and the like; an alkoxycarbonyl group, such as methoxypropionyl and the like; a substituted alkoxycarbonyl group, such as monochloromethylcarbonyl, dichloromethylcarbonyl, trichloromethylcarbonyl, trichloroethylcarbonyl, trichloropropylcarbonyl, trifluoromethylcarbonyl and the like; a substituted arylalkoxycarbonyl group, such as 4-nitrobenzyloxycarbonyl and the like; a benzyl group; a substituted benzyl group; an optionally substituted diphenylmethyl group; an optionally substituted trityl group, such as 4-methoxyphenyldiphenylmethyl or di(4-methoxyphenyl)phenylmethyl; or a silylating group, such as trimethylsilyl or ethyl-dimethylsilyl or tert-butyldimethylsilyl and the like.

The said protective groups can be removed according to conventional methods, for example by reduction or hydrolysis. A more detailed description of these amino-protective groups and the methods for their preparation and their removal are given, for example, by T. W. Greene, "Protective Groups in Organic Synthesis", John Wiley & Sons, 1981 and by J. F. W. McOmie, "Protective Groups in Organic Chemistry", Plenum Press, 1973.

These protective groups are removed according to the standard methods described for the protective group chosen; in the case of tert-butoxycarbonyl, by the removal, the cleavage is normally carried out by acid hydrolysis.

The compounds of formula (I) have shown a powerful activity with respect to $\beta_3$-adrenergic receptors. In addition, these compounds have very little toxicity; in particular, their acute toxicity is compatible with their use as medicaments for the treatment of diseases in which use is made of compounds having affinity for the $\beta_3$ receptor.

The activity of the compounds of the present invention with respect to the $\beta_3$ activity was demonstrated using in vitro tests on the human colon according to the method described in EP-B-436 435 and in T. Croci et al., Br. J. Pharmacol., 1997, 122, 139P.

More particularly, it has been found that the compounds of formula (I) are much more active on the isolated colon than on the atrium and on the trachea.

These surprising properties of the compounds of formula (I) make it possible to envisage their use as medicaments with a $\beta_3$ action.

The compounds of formula (I) and their pharmaceutically acceptable salts may therefore be indicated, for example, in the treatment of gastro-intestinal diseases, such as irritable bowel syndrome, as modulators of intestinal motricity, as lipolytic agents, antiobesity agents, antidiabetics, psychotropics, antiglaucoma agents, cicatrizants or antidepressants, or as tocolytics for preventing or delaying premature labor or for the treatment and/or prophylaxis of dysmenorrhea.

The use of the compounds of formula (I) above, and that of their pharmaceutically acceptable salts and solvates, for the preparation of above medicaments constitutes a subsequent aspect of the present invention.

For such a use, an effective amount of a compound of formula (I) or of one of its pharmaceutically acceptable salts and solvates is administered to the mammals who require such a treatment.

The compounds of formula (I) above and their pharmaceutically acceptable salts and solvates can be used at daily doses of 0.01 to 20 mg per kilo of body weight of the mammal to be treated, preferably at daily doses of 0.1 to 10 mg/kg. In man, the dose can preferably vary from 0.5 mg to 1 500 mg per day, in particular from 2.5 to 500 mg, according to the age of the subject to be treated, the type of treatment, prophylactic or curative, and the seriousness of the condition. The compounds of formula (I) are generally administered as a dosage unit of 0.1 to 500 mg, preferably of 0.5 to 100 mg, of active principle, one to five times daily.

Said dosage units are preferably formulated in pharmaceutical compositions in which the active principle is mixed with a pharmaceutical excipient.

Thus, according to another of its aspects, the present invention relates to pharmaceutical compositions including, as active principle, a compound of formula (I) above or one of its pharmaceutically acceptable salts and solvates.

In the pharmaceutical compositions of the present invention for oral, sublingual, subcutaneous, intramuscular, intravenous, topical, transdermal or rectal administration, the active principles of formula (I) above and their pharmaceutically acceptable salts and solvates can be administered in unit administration forms, as a mixture with conventional pharmaceutical vehicles, to animals and human beings for the treatment of the above said conditions. The appropriate unit administration forms comprise oral forms, such as tablets, gelatin capsules, powders, granules and solutions or suspensions to be taken orally, sublingual and buccal administration forms, subcutaneous, intramuscular or intravenous administration forms, local administration forms and rectal administration forms.

When a solid composition is prepared in the form of tablets, the main active ingredient is mixed with a pharmaceutical vehicle, such as gelatin, starch, lactose, magnesium stearate, talc, gum arabic or the like. The tablets can be coated with sucrose or other appropriate materials or can be treated so that they have a prolonged or delayed activity and so that they continuously release a predetermined amount of active principle.

A preparation in the form of gelatin capsules is obtained by mixing the active ingredient with a diluent and by pouring the mixture obtained into soft or hard gelatin capsules.

A preparation in the syrup or elixir form can comprise the active ingredient in conjunction with a sweetener, preferably a calorie-free sweetener, methyl-paraben and propylparaben as antiseptics, and an appropriate colorant and flavoring.

The water-dispersible powders or granules can comprise the active ingredient as a mixture with dispersing agents, wetting agents or suspending agents, such as polyvinylpyrrolidone, and with sweeteners or flavor enhancers.

The water-dispersible powders or granules can comprise the active ingredient as a mixture with dispersing agents, wetting agents or suspending agents, such as polyvinylpyrrolidone, and with sweeteners or flavor enhancers.

For local administration, the active principle is mixed in an excipient for the preparation of creams or ointments or is dissolved in a vehicle for intraocular administration, for example in the form of an eyewash.

For rectal administration, recourse is had to suppositories which are prepared with binders which melt at the rectal temperature, for example cocoa butter or polyethylene glycols.

For parenteral administration, use is made of aqueous suspensions, saline solutions or sterile injectable solutions which comprise pharmacologically compatible dispersing and/or wetting agents, for example propylene glycol or butylene glycol.

The active principle can also be formulated in the form of microcapsules, optionally with one or more vehicles or additives.

According to another of its aspects, the present invention relates to a method for the treatment of the pathologies which are improved by a $\beta_3$-agonist action which consists in administering a compound of formula (I) or one of its pharmaceutically acceptable salts or solvates. The compounds of formula (I), in particular the compounds (I) labeled with an isotope, can also be used as laboratory tools in biochemical assays.

The compounds of formula (I) bind to the $\beta_3$-adrenergic receptor. These compounds can therefore be used in a standard binding assay, in which use is made of an organic tissue in which this receptor is particularly abundant, and the amount of compound (I) displaced by a test compound is measured, in order to evaluate the affinity of said compound with respect to binding sites of this specific receptor.

Another specific subject matter of the present invention is thus a reagent which can be used in biochemical assays, which comprises at least one suitably labeled compound of formula (I).

The examples which follow illustrate the invention.

EXAMPLE 1

3-[1-(5-Ethoxycarbonylpyrid-2-yl)-4-piperidinylamino]-[1,2-dihydro-2-oxobenzimidazol-4-yloxy]-2-propanol.

a) 4-(tert-butoxycarbonylamino)piperidine.

25 g (0.13 mol) of 4-amino-1-benzyl-piperidine, 36.2 ml (0.26 mol) of triethylamine and 31.2 g (0.143 mol) of di-tert-butyl dicarbonate in 200 ml of dimethylformamide are mixed at ambient temperature for 2 hours. The mixture is poured into water, extraction is carried out with ethyl acetate, the extract is washed with water and the product thus obtained is crystallized from 200 ml of isopropyl ether. 33 g of 1-benzyl-4-(tert-butoxycarbonylamino)-piperidine are obtained, which product is hydrogenated in a mixture of 200 ml of ethanol and 100 ml of tetra-hydrofuran in the presence of 3 g of 10% Pd/C. After filtering off the catalyst, the title compound is isolated. M.p.: 157–160° C.

b) 4-tert-butoxycarbonylamino-1-(5-ethoxycarbonyl-pyrid-2-yl) piperidine

A mixture of the product prepared above, of triethylamine and of the ethyl ester of 6-chloro-nicotinic acid is heated at 80° C. for 18 hours. After cooling, water is added, extraction is carried out with ethyl acetate, the organic phase is dried over sodium sulfate and the solvent is evaporated under reduced pressure. The title compound is obtained.

M.p. 140–142° C.

c) 4-amino-1-(5-ethoxycarbonylpyrid-2-yl)piperidine (dihydrochloride hydrate)

The product of stage b) is dissolved in ethyl acetate, a 3N solution of hydrochloric acid in ethyl acetate is added and the mixture is left stirring at ambient temperature for 10 hours. The product is filtered off and washed with acetone. The title product is obtained. M.p.: 148–150° C.

d) 2-amino-3-nitro-1-(2,3-epoxypropoxy)benzene 21.7 g (0.095 mol) of glycidyl tosylate, 10 g (0.0475 mol) of 2-amino-3-nitrophenol and 6.5 g of crushed $K_2CO_3$ are mixed in acetone and the mixture is heated at reflux for 18 hours. The mixture is filtered and the solvent is evaporated under reduced pressure. The crude reaction product is purified by flash chromatography, elution being carried out with a 9/1 hexane/ethyl acetate mixture. The title compound is obtained. M.p.: 7°–78° C.

e) 3-[1-(5-ethoxycarbonylpyrid-2-yl)-4-piperidinyl-amino]-1-(2-amino-3-nitrophenoxy)-2-propanol 1 g (0.00475 mol) of the compound obtained in the preceding stage is mixed with 1.53 g (0.00475 mol) of 4-amino-1-(5-ethoxycarbonylpyrid-2-yl)piperidine (stage c, base) in 50 ml of ethanol. The mixture is refluxed overnight and is evaporated under reduced pressure. The crude reaction product is purified by flash chromatography, elution being carried out with a 9/1 ethyl acetate/ethanol mixture. The title compound is obtained.

M.p.: 140–142° C.

f) 3-[1-(5-ethoxycarbonylpyrid-2-yl)-4-piperidinyl-amino]-1-(2,3-diaminophenoxy)-2-propanol 1.71 g (0.0037 mol) of the compound of the preceding stage are hydrogenated at ambient temperature in 120 ml of ethanol in the presence of 0.8 g of 5% Pd/C. After having filtered and evaporated the solvent, the crude reaction product is purified by flash chromatography, elution being carried out with a 7/3 ethyl acetate/ethanol mixture. The title compound is obtained.

g) 3-[1-(5-ethoxycarbonylpyrid-2-yl)-4-piperidinyl-amino]-1-[1,2-dihydro-2-oxobenzimidazol-4-yloxy]-2-propanol The product obtained in the preceding stage is placed with 0.44 g of N,N-carbonyldiimidazole (0.027 mol) in 50 ml of THF with stirring at ambient temperature overnight. The solvent is evaporated under reduced pressure, ethyl acetate is added and washing is carried out with water. After drying and evaporating the solvent, a first purification by chromatography is carried out, elution being carried out with an 8/2 methylene chloride/methanol mixture, and a second purification by chromatography is carried out, elution being carried out with an 8/2 methanol/ethyl acetate mixture. The title product is obtained.

M.p.: 191°–193° C.

EXAMPLE 2

3-[1-(5-Ethoxycarbonylpyrid-2-yl)-4-piperidinylamino]-[2-aminopyrid-5-yloxy]-2-propanol a) 2-[2-(4-nitrophenyl)diazenyl]-5-(2,3-epoxy-propoxy)pyridine 1.64 ml of diethyl azodicarboxylate (0.01043 mol) are added at 0° C., under a nitrogen atmosphere, to a solution containing 1.82 g of 5-hydroxy-2-(2-(4-nitrophenyl)diazenyl)pyridine (0.01043 mol), prepared according to the method described in J. Am. Chem. Soc., 1959, 81, 6049, 0.692 ml of 2,3-epoxypropanol (0.01043 mol) and 2.74 g of $Ph_3P$ (0.01043 mol) in 18 ml of DMF. The mixture is allowed to react for one hour at 0° C. and then for 40 hours at ambient temperature with stirring. Water is added, extraction is carried out with ethyl acetate, the extract is washed and the solvent is evaporated. The crude reaction product is purified by chromatography, elution being carried out with a 100/2 $CH_2Cl_2/CH_3OH$ mixture. The title product is obtained.

M.p.: 150–152° C. (dec.).

b) 3-[1-(5-ethoxycarbonylpyrid-2-yl)-4-piperidinyl-amino]-1-[2-(2-(4-nitrophenyl)diazenyl)pyrid-5-yloxy]-2-propanol A solution of 1.15 g (0.00383 mol) of the product obtained in stage a) and 1.05 g (0.00421 mol) of 1-(5-ethoxycarbonylpyrid-2-yl)-4-piperidylamine in 20 ml of ethanol is heated at reflux for 7 hours. Filtration is carried out, drying is carried out and crystallization is carried out from a solution of ethanol and $CH_2Cl_2$. The title product is obtained.

M.p.: 172° C.

c) 3-[1-(5-ethoxycarbonylpyrid-2-yl)-4-piperidinyl-amino]-1-[2-aminopyrid-5-yloxy]-2-propanol 1.37 g (0.002509 mol) of the product of stage c) are dissolved with 0.16 g of Pd/C in 30 ml of ethanol and 2 ml of $CH_3COOH$ (d=1.049, 0.0347 mol). The mixture is hydrogenated for 9 hours with stirring at a temperature of between 15 and 20° C. The crude reaction product is filtered through celite and washed with ethanol. The solvent is evaporated, 30 ml of a saturated $NaHCO_3$ solution and 5 ml of 1N NaOH are added, and extraction is carried out with ethyl acetate. The solvent is evaporated and the crude reaction product is purified by chromatography, elution being carried out with a 95/5/0.5 and subsequently 90/10/1 $CH_2Cl_2/CH_3OH/NH_4OH$ mixture.

The title product is obtained. M.p.: 120–122° C.

EXAMPLE 3

3-[1-(5-Ethoxycarbonylpyrid-2-yl)-4-piperidinylamino]-1-(1,2-dihydro-2-oxobenzimidazol-4-yloxy)-(2S)-2-propanol a) 2-Amino-3-nitro-1-((2S)-2,3-epoxypropoxy)benzene 5 g (0.032 mol) of 2-amino-3-nitrophenol, 8 g (0.032 mol) of (S)-(+)-glycidyl 3-nitrobenzenesulfonate and 8.9 g of $K_2CO_3$ are mixed in 80 ml of acetone and the mixture is refluxed for 18 hours. Filtration is carried out, the solvent is evaporated under reduced pressure and the crude product is purified by flash chromatography, elution being carried out with a 7/3 cyclohexane/ethyl acetate mixture. The solid product obtained is triturated in ethyl ether and 5.67 g of the title product are obtained. M.p.: 107–109°. $\alpha_D$+28.1 (c=0.5%, MeOH).

b) 3-[1-(5-ethoxycarbonylpyrid-2-yl)-4-piperidinidylamino]-1-(2-amino-3-nitrophenoxy)-(2S)-2-propanol By following the method of example 1 e) but starting from the compound prepared above, the title product is obtained. $\alpha_D$=+18.3 (c=1% MeOH)

c) 3-[1-(5-ethoxycarbonylpyrid-2-yl)-4-piperidinidylamino]-1-(2,3-diaminophenoxy)-(2S)-2-propanol By following the method of example 1 f) but starting from the compound prepared above, the title product is obtained.

d) 3-[1-(5-ethoxycarbonylpyrid-2-yl)-4-piperidinyl-amino]-1-(1,2-dihydro-2-oxobenzimidazol-4-yloxy)-(2S)-2-propanol 0.3 g (0.061 mol) of the product obtained in stage c) is placed in 4 ml of toluene and 4 ml of water with 0.059 (0.488 mol) of trichloromethyl chloroformate with stirring at ambient temperature for 4 hours. Filtration is carried out, the product is dissolved in ethanol and aqueous ammonia, the solvent is evaporated, purification is carried out by flash chromatography, elution being carried out with a 90/10/1 methylene chloride/methanol/aqueous ammonia mixture, and the title product is obtained. Amorphous solid.

200 MHz ($^1$H) and 50 MHz ($^{13}$C) NMR Spectrum:

$^1$H NMR (aromatics)—V$_{TMS}$ (CDCl$_3$, ppm): 6.3–6.6 (3H, m), 6.6–6.9 (1H, m), 7.91 (1H, dd, J$_1$ 9 Hz, J$_2$ 2 Hz), 8.72 (1H, d, J 2 Hz).

$^{13}$C NMR—V$_{TMS}$ (CDCl$_3$, ppm): 14.3, 31.6, 31.7, 43.5, 48.6, 55.1, 60.3, 69.0, 71.3, 103.2, 105.0, 114.3, 118.9, 121.7, 129.9, 138.3, 143.2, 150.9, 156.7, 160.2, 165.9.

EXAMPLE 4

3-[1-(4-Ethoxycarbonylphenyl)-4-piperidinylamino]-1-(1,2-dihydro-2-oxobenzimidazol-4-yloxy)-(2S)-2-propanol a) 4-(tert-butoxycarbonylamino)piperidine 25 g (0.13 mol) of 4-amino-1-benzyl-piperidine, 36.2 ml (0.26 mol) of triethylamine and 31.2 g (0.143 mol) of di-tert-butyl dicarbonate are mixed in 200 ml of dimethylformamide at ambient temperature for 2 hours. The mixture is poured into water, extraction is carried out with ethyl acetate, the extract is washed with water and the product thus obtained is crystallized from 200 ml of isopropyl ether. 33 g of 1-benzyl-4-(tert-butoxycarbonylamino)-piperidine are obtained, which product is hydrogenated in a mixture of 200 ml of ethanol and 100 ml of tetra-hydrofuran in the presence of 3 g of 10% Pd/C. After filtering off the catalyst, the title compound is isolated.

M.p.: 157–160° C.

b) 4-tert-butoxycarbonylamino-1-(4-ethoxycarbonyl-phenyl)piperidine 21.6 g (0.10 mol) of the product obtained above are heated at 80° C. for 55 hours with 9.06 g (0.01 mol) of 4-ethoxycarbonyl-1-fluorobenzene and 14.9 g of $K_2CO_3$ in 200 ml of dimethylformamide. The $K_2CO_3$ is filtered off, the solution is poured into water, extraction is carried out with ethyl acetate and the solvent is evaporated. The crude reaction product is purified by flash chromatography, elution being carried out with an 8/2 cyclohexane/ethyl acetate mixture. The title product is obtained and is crystallized from ethyl acetate. M.p.=138°–140°.

c) 4-amino-1-(4-ethoxycarbonylphenyl)piperidine (hydrochloride)

9.74 g (0.023 mol) of the product obtained in c) are dissolved in 60 ml of ethyl acetate, and 80 ml of a 3N solution of HCl in ethyl acetate are added. Heating at reflux is carried out for 5 hours, the solvent is evaporated, acetone is added and the product is filtered off. The title product is obtained and is crystallized with ethanol. M.p.: 240–242°.

d) 3-[1-(4-ethoxycarbonylphenyl)-4-piperidinyl-amino]-1-(2-amino-3-nitrophenoxy)-(2S)-propanol By following the method of example 1 e) but using 1 g (0.0040 mol) of the compound obtained above (base) and 0.85 g (0.0040 mol) of the epoxide of example 3 a), 1.24 g of the title product are obtained, after purification by flash chromatography with a 95/5 methylene chloride/methanol mixture.

M.p.: 112-114°.

e) 3-[1-(4-ethoxycarbonylphenyl)-4-piperidinylamino]1-(2,3-diaminophenoxy)-(2S)-propanol By following the method of Example 1 f) but starting from 1.2 g (0.0026 mol) of the compound obtained above, 1.2 g of the title product are obtained.

f) 3-[1-(4-ethoxycarbonylphenyl)-4-piperidinylamino]-1-(1,2-dihydro-2-oxobenzimidazol-4-oxy)-(2S)-propanol The product obtained in the preceding stage is placed with 0.57 g (0.0029 mol) of trichloromethyl chloroformate in 20 ml of toluene and 20 ml of tetra-hydrofuran (THF) with stirring at ambient temperature for 4 hours; The solvent is evaporated under reduced pressure, ethyl acetate and aqueous ammonia are added, and washing is carried out with water. The organic phase is dried over sodium sulfate, the solvent is evaporated and the residue is purified by flash chromatography, elution being carried out with an 8/2 methanol/ethyl acetate mixture. 0.72 g of the title product is obtained.

M.p.: 188–190°. $\alpha$365=+41.5 (c=1%, MeOH).

EXAMPLE 5

3-[1-(4-n-Butylaminocarbonylphenyl)-4-piperidinyl-amino]-1-(1,2-dihydro-2-oxobenzimidazol-4-oxy)-(2S)-propanol a) 4-tert-butoxycarbonylamino-1-(4-hydroxycarbonyl-phenyl)piperidine 2.19 g (0.0063 mol) of the product of example 4 b) are dissolved in 30 ml of THF and 20 ml of water, and 12.6 ml (0.0126 mol) of 1N NaOH are added. After 24 hours at ambient temperature, acetic acid is added until a pH of 7 is achieved, the solvent is evaporated, and the solid thus obtained is triturated in water, filtered off and crystallized from ethanol. 1.32 g of the title compound are obtained. M.p. >300°.

b) 4-tert-butoxycarbonylamino-1-(4-n-butylamino-carbonylphenyl)piperidine 2.5 g (0.0078 mol) of the product from the preceding stage, 3.45 g (0.0078 mol) of (benzotriazol-1-yloxy)tris (dimethylamino)phosphonium hexafluoro-phosphate, 0.57 g (0.0078 mol) of n-butylamine and 1.7 ml (0.012 mol) of triethylamine are mixed in 80 ml of methylene chloride and the mixture is heated at 40° for 8 hours. The solvent is evaporated and ethyl acetate and a saturated NaHCO$_3$ solution are added. A solid in suspension is obtained, which solid is filtered off and washed with water and then with ethyl acetate. The product is crystallized from 50 ml of isopropanol and 2.14 g of the title product are obtained. M.p.: 208–210°.

c) 4-amino-1-(4-n-butylaminocarbonylphenyl)piperidine (hydrochloride dihydrate)

By following the method of example 4 c) but using the compound from the preceding stage as starting material, 1.66 g of the title product are obtained, after crystallization from ethanol. M.p.: 231–235°.

d) 3-[1-(4-n-butylaminocarbonylphenyl)-4-piperidinylamino]-1-(2-amino-3-nitrophenoxy)-(2S)-propanol By using 0.49 g (0.0018 mol) of the product from the preceding example (base) and 0.4 g (0.0019 mol) of the epoxide of example 3a) in 20 ml of ethanol and by following the method of example 1e), 0.57 g of the title compound is obtained, after purification by flash chromatography with a 100/1 methanol/aqueous ammonia mixture. M.p. 68–70°.

e) 3-[1-(4-n-butylaminocarbonylphenyl)-4-piperidinylamino]-1-(2,3-diaminophenoxy)-(2S)-propanol By carrying out the preparation as in example 1 f) but using the compound obtained above as starting material, 0.52 g of the title product is obtained.

f) 3-[1-(4-n-butylaminocarbonylphenyl)-4-piperidinylamino]-1-(1,2-dihydro-2-oxobenzimidazol-4-oxy)-(2S)-propanol The product obtained in the preceding stage is placed with 0.23 g (0.0012 mol) of trichloromethyl chloroformate in 20 ml of THF and 4 ml of methylene chloride with stirring at ambient temperature for 4 hours. The solvent is evaporated under reduced pressure, ethyl acetate and aqueous ammonia are added, and washing is carried out with water. The organic phase is dried over sodium sulfate, the solvent is evaporated and the residue is purified by flash chromatography, elution being carried out with a 3/7 methanol/ethyl acetate mixture. 0.052 g of the title compound is obtained. M.p.: 82–84°.

What is claimed is:

1. A compound of formula (I):

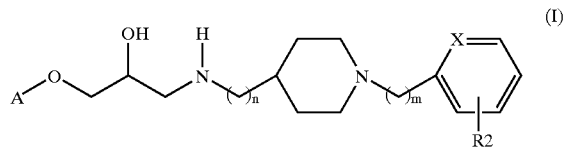

(I)

where

X is N or CH;

A represents a group of formula (a) or (b)

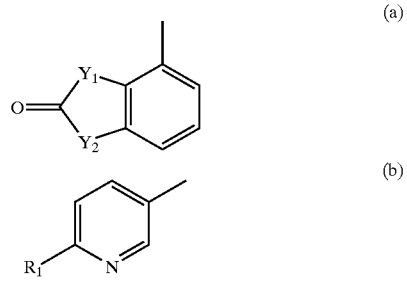

$R_1$ represents a hydrogen atom or an —NH$_2$, —NR$_3$R$_4$, —NR$_3$CO(C$_1$–C$_4$)Alk or —NR$_3$SO$_2$(C$_1$–C$_4$)Alk group;

$R_2$ represents a hydrogen or halogen atom or a (C$_1$–C$_4$)Alk, (C$_1$–C$_4$)alkoxy, —COOH, —COO(C$_1$–C$_4$)Alk, —CN, —CONR$_3$R$_4$, —NO$_2$, or —NHSO$_2$(C$_1$–C$_4$)Alk group;

m and n each represent 0, 1 or 2;

$R_3$ and $R_4$ each represent a hydrogen atom or a (C$_1$–C$_4$)Alk group;

$Y_1$ and $Y_2$ each represent NH or O;

or a salt or solvate thereof.

2. A compound as claimed in claim 1, where X represents CH.

3. A compound as claimed in claim 1, where X represents a nitrogen atom and the $R_2$ group is in the 5-position.

4. A compound as claimed in claim 1, where the (C$_1$–C$_4$) Alk group is a methyl or ethyl group.

5. A compound as claimed in claim 1, where $R_2$ is chosen from —COOH, —COO(C$_1$–C$_4$)Alk, —CN, —NO$_2$, —CONR$_3$R$_4$ and —NHSO$_2$-(C$_1$–C$_4$)Alk.

6. 3-[1-(5-Ethoxycarbonylpyrid-2-yl)-4-piperidinylamino]-1-(1,2-dihydro-2-oxobenzimidazol-4-yloxy)-2-propanol or a salt or solvate thereof.

7. 3-[1-(5-Ethoxycarbonylpyrid-2-yl)-4-piperidinylamino]-1-[2-aminopyrid-5-yloxy]-2-propanol or a salt or solvate thereof.

8. A process for the preparation of the compound of claim 1 wherein an epoxide of formula (II):

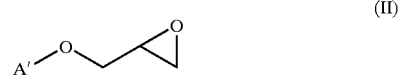

(II)

in which A' represents the group (a) or the group (b) in which $R_1$ is optionally protected, where (a), (b) and $R_1$ are as defined in claim 1, is reacted with an amine of formula (III)

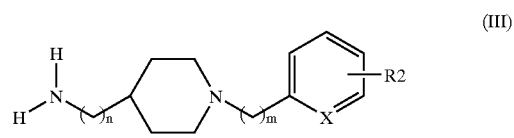

(III)

where m, n, $R_2$ and X are as indicated above, the protective group optionally present is removed and, optionally, the product of formula (I) thus obtained is converted into one of its salts or solvates.

9. A process for the preparation of the compound of claim 1 where A represents a group (b) and $R_1$ is an NH$_2$ group, wherein a product of formula (II) as defined in claim 8 where A' is the group (b) and $R_1$ is a group of formula:

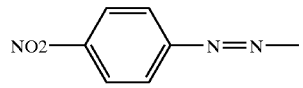

is reacted with an amine of formula III and the product of formula IV thus obtained:

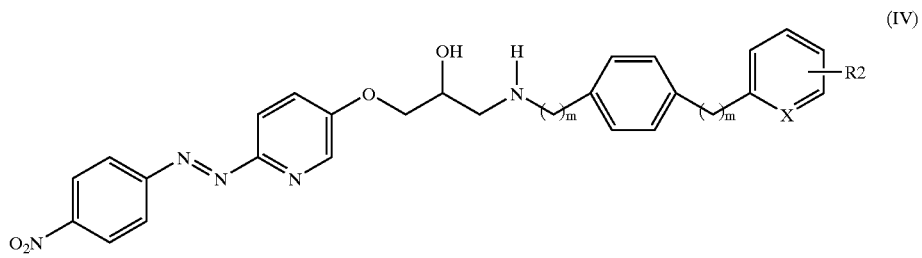

(IV)

is subjected to a hydrogenation reaction in order to convert the 4-nitrophenyldiazenyl group to an amino group and, optionally, the product of formula (I) thus obtained is converted into one of its salts or solvates.

10. A process for the preparation of the compound of claim 1 where A represents the group (a) and $Y_1$ and $Y_2$ represent a nitrogen atom, wherein a compound of formula (V):

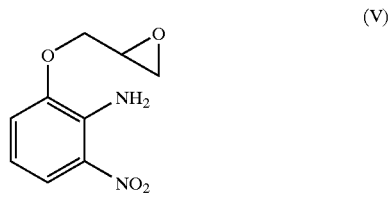

(V)

is reacted with a compound of formula (III) as defined in claim 8, the nitro group of the product of formula (VI) thus obtained:

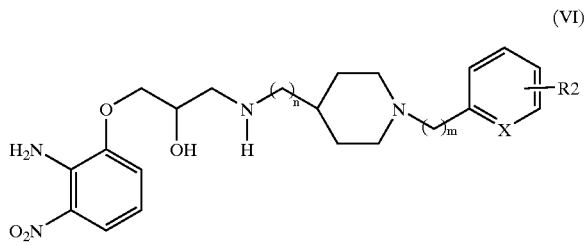

(VI)

is reduced, the product of formula (VII) thus obtained:

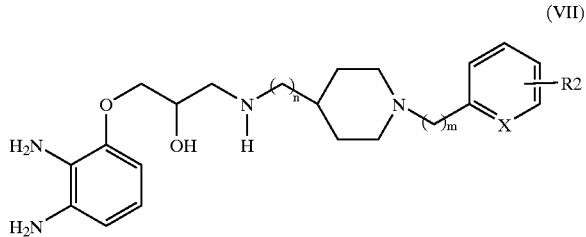

(VII)

is treated with a carbonylation agent, the product of formula (I) thus obtained is isolated and, optionally, is converted into one of its salts or solvates.

11. A process as claimed in claim 10 wherein the carbonylation agent is chosen from carbonyldiimidazole and phosgene.

12. A pharmaceutical composition comprising an effective amount of at least one compound of claim 1 as active principle.

13. A pharmaceutical composition comprising an effective amount of a compound according to claim 2.

14. A pharmaceutical composition comprising an effective amount of a compound according to claim 3.

15. A pharmaceutical composition comprising an effective amount of a compound according to claim 4.

16. A pharmaceutical composition comprising an effective amount of a compound according to claim 5.

17. A pharmaceutical composition comprising an effective amount of a compound according to claim 6.

18. A pharmaceutical composition comprising an effective amount of a compound according to claim 7.

19. A method for treating irritable bowel syndrome, for treating obesity, for treating diabetes, for treating glaucoma, for preventing or delaying premature labor, or for the treatment or prophylaxis of dysmenorrhea which comprises administering to a patient in need of such treatment an effective amount of a compound according to claim 1.

20. A method for treating irritable bowel syndrome, for treating obesity, for treating diabetes, for treating glaucoma, for preventing or delaying premature labor, or for the treatment or prophylaxis of dysmenorrhea which comprises administering to a patient in need of such treatment an effective amount of a compound according to claim 2.

21. A method for treating irritable bowel syndrome, for treating obesity, for treating diabetes, for treating glaucoma, for preventing or delaying premature labor, or for the treatment or prophylaxis of dysmenorrhea which comprises administering to a patient in need of such treatment an effective amount of a compound according to claim 3.

22. A method for treating irritable bowel syndromey, for treating obesity, for treating diabetes, for treating glaucoma, for preventing or delaying premature labor, or for the treatment or prophylaxis of dysmenorrhea which comprises administering to a patient in need of such treatment an effective amount of a compound according to claim 4.

23. A method for treating irritable bowel syndrome, for treating obesity, for treating diabetes, for treating glaucoma, for preventing or delaying premature labor, or for the treatment or prophylaxis of dysmenorrhea which comprises administering to a patient in need of such treatment an effective amount of a compound according to claim 5.

24. A method for treating irritable bowel syndrome, for treating obesity, for treating diabetes, for treating glaucoma, for preventing or delaying premature labor, or for the treatment or prophylaxis of dysmenorrhea which comprises administering to a patient in need of such treatment an effective amount of a compound according to claim 6.

25. A method for treating irritable bowel syndrome, for treating obesity, for treating diabetes, for treating glaucoma, for preventing or delaying premature labor, or for the treatment or prophylaxis of dysmenorrhea which comprises administering to a patient in need of such treatment an effective amount of a compound according to claim 7.

\* \* \* \* \*

UNITED STATES PATENT AND TRADEMARK OFFICE
CERTIFICATE OF CORRECTION

PATENT NO. : 6,858,629 B1 Page 1 of 1
APPLICATION NO. : 10/070453
DATED : February 22, 2005
INVENTOR(S) : Cecchi et al.

It is certified that error appears in the above-identified patent and that said Letters Patent is hereby corrected as shown below:

Column 6, line 52: please delete "The water-dispersible powders or granules can comprise the active ingredient as a mixture with dispersing agents, wetting agents or suspending agents, such as polyvinylpyrrolidone, and with sweeteners or flavor enhancers."

Column 7, line 67: "7°-78°" should read as -- 76°-78° --.

Column 8, line 35: "piperidinylamino]-[2" should read as -- piperidinylamino]-1-[2 --.

Column 14, line 42: "irritable bowel syndromey" should read as -- irritable bowel syndrome --.

Signed and Sealed this

Twentieth Day of November, 2007

JON W. DUDAS
*Director of the United States Patent and Trademark Office*